US00PP24473P2

(12) United States Plant Patent
Shishido

(10) Patent No.: US PP24,473 P2
(45) Date of Patent: May 20, 2014

(54) ***DIANTHUS* PLANT NAMED 'SHISHIKA-02'**

(50) Latin Name: *Dianthus speciosus*
Varietal Denomination: Shishika-02

(75) Inventor: Kazuyuki Shishido, Yokoshibahikari-machi (JP)

(73) Assignee: Amerinova Properties LLC, Bonsall, CA (US)

( * ) Notice: Subject to any disclaimer, the term of this patent is extended or adjusted under 35 U.S.C. 154(b) by 65 days.

(21) Appl. No.: 13/507,512

(22) Filed: Jul. 5, 2012

(51) Int. Cl.
*A01H 5/00* (2006.01)

(52) U.S. Cl.
USPC ..... Plt./281; Plt./272

(58) Field of Classification Search
USPC ..... Plt./272, 281
See application file for complete search history.

*Primary Examiner* — Susan McCormick Ewoldt
(74) *Attorney, Agent, or Firm* — C. A. Whealy

(57) ABSTRACT

A new and distinct cultivar of *Dianthus* plant named 'Shishika-02', characterized by its compact, upright and uniformly mounding plant habit; vigorous growth habit; short internodes and freely branching habit; light purple to light violet-colored flowers with white-colored centers that are positioned above and beyond the foliar plane; and good garden performance.

1 Drawing Sheet

Botanical designation: *Dianthus speciosus*.
Cultivar denomination: 'SHISHIKA-02'.

BACKGROUND OF THE INVENTION

The present invention relates to a new and distinct cultivar of *Dianthus* plant, botanically known as *Dianthus speciosus*, grown as a garden plant and hereinafter referred to by the name 'Shishika-02'.

The new *Dianthus* plant is a product of a planned breeding program conducted by the Inventor in Chiba, Japan. The objective of the breeding program was to develop new freely branching and freely flowering *Dianthus* plants with attractive flower coloration.

The new *Dianthus* plant is a naturally-occurring branch mutation of *Dianthus speciosus* 'Kahori', not patented. The new *Dianthus* plant was discovered and selected by the Inventor on a single flowering plant within a population of plants of 'Kahori' in a controlled greenhouse environment in Chiba, Japan in November, 2006.

Asexual reproduction of the new *Dianthus* plant by terminal cuttings propagated in a controlled environment in Chiba, Japan since December, 2006 has shown that the unique features of this new *Dianthus* plant are stable and reproduced true to type in successive generations of asexual reproduction.

SUMMARY OF THE INVENTION

Plants of the new *Dianthus* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Shishika-02'. These characteristics in combination distinguish 'Shishika-02' as a new and distinct *Dianthus* plant:

1. Compact, upright and uniformly mounding plant habit.
2. Vigorous growth habit.

3. Short internodes and freely branching habit.
4. Light purple to light violet-colored flowers with white-colored centers that are positioned above and beyond the foliar plane.
5. Good garden performance.

Plants of the new *Dianthus* differ primarily from plants of the branch mutation parent, 'Kahori', in flower color as plants 'Kahori' have red purple-colored flowers. In addition, plants of the new *Dianthus* and 'Kahori' differ in flower shape.

Plants of the new *Dianthus* can be compared to plants of the *Dianthus speciosus* 'Shishi-01', disclosed in U.S. Plant patent application Ser. No. 12/069,042 (now abandoned). In side-by-side comparisons conducted in Chiba, Japan, plants of the new *Dianthus* differed from plants of 'Shishi-01' in the following characteristics:

1. Plants of the new *Dianthus* were larger than and not as compact as plants of 'Shishi-01'.
2. Plants of the new *Dianthus* were more freely branching than plants of 'Shishi-01'.
3. Plants of the new *Dianthus* and 'Shishi-01' differed in flower color as plants of 'Shishi-01' had red purple-colored flowers.

BRIEF DESCRIPTION OF THE PHOTOGRAPHS

The accompanying photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the colors of the new *Dianthus* plant.

The photograph at the bottom of the sheet comprises a side perspective view of typical flowering plants of 'Shishika-02' grown in a container.

The photograph at the top of the sheet is a close-up view of typical flowers of 'Shishika-02'.

DETAILED BOTANICAL DESCRIPTION

The aforementioned photographs and following observations and measurements describe plants grown during the early spring in one-gallon containers in a polyethylene-covered greenhouse in Bonsall, Calif. under cultural practices which approximate those generally used in commercial *Dianthus* production. During the production of the plants, day temperatures ranged from 16° C. to 24° C., night temperatures ranged from 4° C. to 10° C. and light levels ranged from 4,200 to 5,000 foot-candles. Plants were pinched one time at planting. Plants were three months old when the photographs and the detailed description were taken. In the following description, color references are made to The Royal Horticultural Society Colour Chart, 2007 Edition, except where general terms of ordinary dictionary significance are used.

Botanical classification: *Dianthus speciosus* 'Shishika-02'.

Parentage: Naturally-occurring branch mutation of *Dianthus speciosus* 'Kahori', not patented.

Propagation:

*Type.*—Terminal cuttings.

*Time to initiate roots, summer.*—About two to three weeks at 22° C. to 27° C.

*Time to initiate roots, winter.*—About three to four weeks at 18° C. to 23° C.

*Time to produce a rooted young plant, summer.*—About four weeks at 22° C. to 27° C.

*Time to produce a rooted young plant, winter.*—About six weeks at 18° C. to 23° C.

*Root description.*—Medium in thickness, fibrous; white in color.

*Rooting habit.*—Moderate branching; medium density.

Plant description:

*Plant and growth habit.*—Compact, upright and mounding plant habit; freely clumping; vigorous growth habit.

*Plant height.*—About 20 cm.

*Plant diameter* (*spread*).—About 30 cm.

*Lateral branch description.*—Branching habit: Freely-branching growth habit with about 85 primary lateral branches each with about three to four secondary lateral branches developing per plant; pinching enhances lateral branch development; dense and bushy growth habit. Length: About 16 cm. Diameter: About 2 mm. Internode length: About 2.6 cm. Texture: Smooth, glabrous. Color: Close to 147A.

*Foliage description.*—Arrangement: Opposite, simple; sessile. Length: About 5.8 cm. Width: About 4 mm. Shape: Lanceolate. Apex: Acute. Base: Attenuate, clasping. Margin: Entire. Texture, upper and lower surfaces: Smooth, glabrous; tough. Venation pattern: Parallel. Color: Developing leaves, upper and lower surfaces: Close to 137B. Fully expanded leaves, upper surface: Close to N137C; venation, close to N137C. Fully expanded leaves, lower surface: Close to N137D; venation, close to N137D.

Flower description:

*Flower type and flowering habit.*—Single star-shaped terminal and axillary flowers with fringed margins; freely flowering with typically seven to eight flowers developing per lateral shoot; flowers positioned above and beyond the foliar plane; flowers face upright.

*Fragrance.*—Faintly fragrant; sweet.

*Natural flowering season.*—Flowering is continuous from spring to fall in Southern California.

*Flower longevity.*—Flowers last about five days on the plant; flowers persistent.

*Flower diameter.*—About 2.2 cm.

*Flower depth.*—About 2.4 cm.

*Flower buds.*—Length: About 1.4 cm. Diameter: About 4 mm. Shape: Oblong, slender. Color: Close to 76B to 76C.

*Petals.*—Quantity and arrangement: About five arranged in a single whorl. Length: About 2.5 cm. Width: At the apex, about 1.2 cm; at the base, about 1.5 mm. Shape: Roughly obdeltoid. Apex: Rounded; praemorse. Base: Attenuate. Margin: Entire. Texture, upper and lower surfaces: Smooth, glabrous; velvety. Color: When opening, upper surface: Close to 76C; at the margins, close to 75C. When opening, lower surface: Close to 76C to 76D. Fully opened, upper surface: Close to 84B to 84C; towards the base, close to 155A; color becoming closer to 76C with development. Fully opened, lower surface: Close to 75C to 75D; towards the base, close to 155D; color becoming closer to 76D with development.

*Sepals.*—Quantity and arrangement: Five fused at the base and arranged in a single whorl. Length: About 1.2 mm. Width: About 2 mm. Shape: Narrowly lanceolate. Apex: Acuminate. Margin: Entire. Texture, upper and lower surfaces: Smooth, glabrous. Color, upper surface: Close to 146C. Color, lower surface: Close to 147B.

*Peduncles.*—Length: About 4.5 cm. Diameter: About 1 mm. Strength: Strong. Orientation: Upright to about 15° from vertical. Texture: Smooth, glabrous. Color: Close to 137A.

*Reproductive organs.*—Stamens: Quantity: About ten per flower. Filament length: About 3 mm. Filament color: Close to 155B. Anther length: Less than 1 mm. Anther shape: Oblong. Anther color: Close to 158A. Pollen amount: None observed. Pistils: Quantity: One per flower. Pistil length: About 2 cm. Stigma shape: Bi-parted. Stigma color: Close to 76A to 76B. Style length: About 1.1 cm. Style color: Close to NN155D. Ovary color: Close to 145B.

*Seeds and fruits.*—Seed and fruit development have not been observed on plants of the new *Dianthus*.

Disease & pest resistance: Plants of the new *Dianthus* have not been observed to be resistant to pathogens and pests common to *Dianthus* plants.

Garden performance: Plants of the new *Dianthus* have been observed to have good garden performance and to tolerate wind, rain and to be hardy to USDA Hardiness Zone 6.

It is claimed:

1. A new and distinct *Dianthus* plant named 'Shishika-02' as illustrated and described.

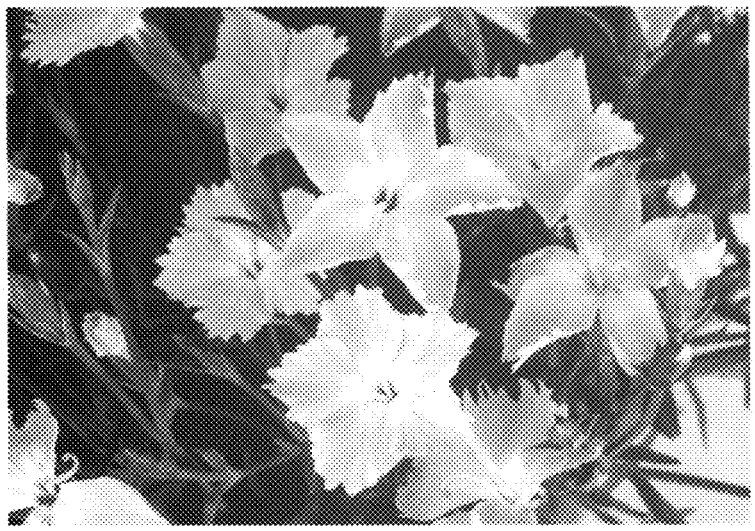
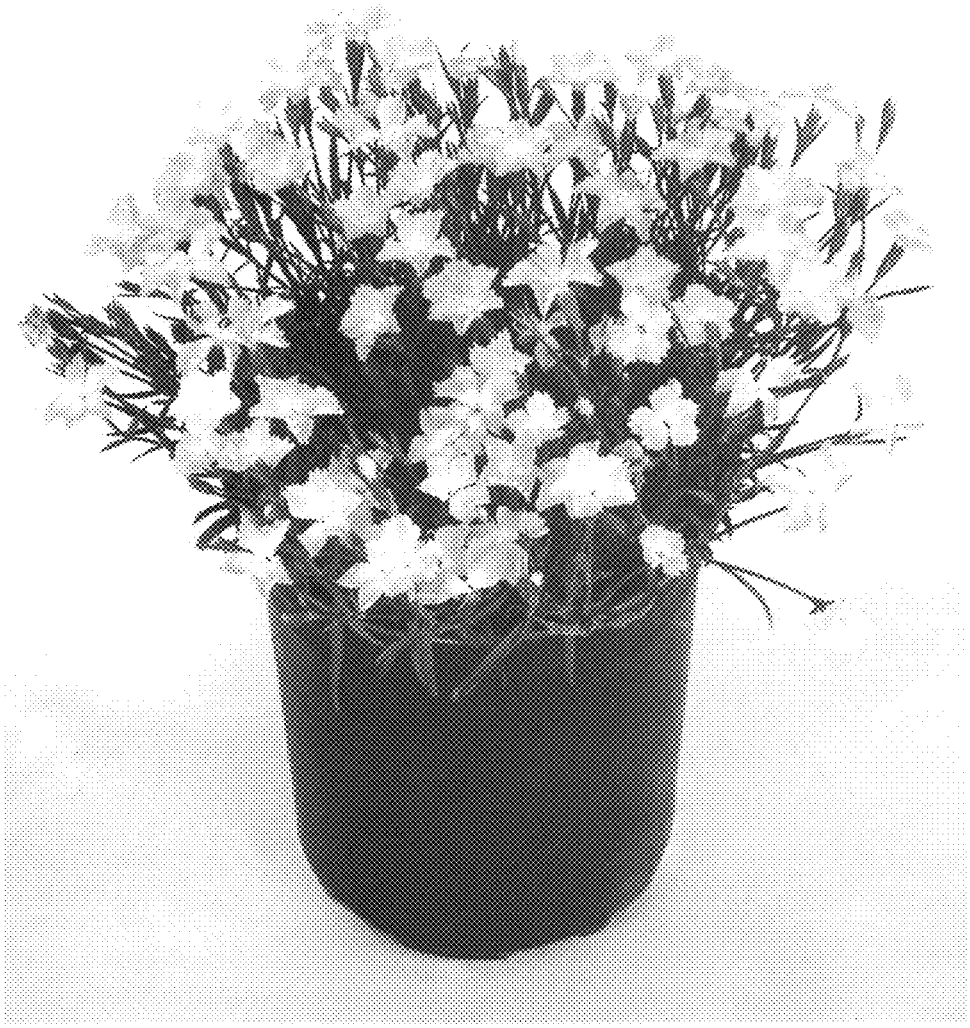

* * * * *